United States Patent [19]
Eaton et al.

[11] Patent Number: 5,964,747
[45] Date of Patent: Oct. 12, 1999

[54] LIGHTING INSTRUMENT, IN PARTICULAR FOR USE IN OPHTHALMOLOGIC MICROSURGERY

[75] Inventors: Alexander M. Eaton, Fort Myers, Fla.; Robert Machemer, Durham, N.C.; Dyson Hickingbotham, Kennesaw, Ga.; Ron Overaker, Durham, N.C.

[73] Assignee: Duke University, Durham, N.C.

[21] Appl. No.: 09/046,162

[22] Filed: Mar. 23, 1998

[51] Int. Cl.⁶ .................................................. A61B 17/36
[52] U.S. Cl. .................................. 606/4; 606/15; 606/17
[58] Field of Search ........................... 606/4, 5, 6, 15, 606/17; 362/572, 575

[56] References Cited

U.S. PATENT DOCUMENTS

| | | | |
|---|---|---|---|
| 5,253,312 | 10/1993 | Payne et al. | 606/15 |
| 5,254,114 | 10/1993 | Reed, Jr. et al. | 606/15 |
| 5,335,648 | 8/1994 | Kozawa et al. | 362/572 |
| 5,431,646 | 7/1995 | Vassiliadis et al. | 606/6 |
| 5,437,657 | 8/1995 | Epstein | 606/4 |
| 5,476,461 | 12/1995 | Cho et al. | 606/15 |
| 5,486,171 | 1/1996 | Chou | 606/16 |
| 5,509,917 | 4/1996 | Cecchetti et al. | 606/15 |
| 5,571,099 | 11/1996 | Purcell, Jr. et al. | 606/17 |
| 5,651,783 | 7/1997 | Reynard | 606/4 |
| 5,772,657 | 6/1998 | Hmelar et al. | 606/15 |

*Primary Examiner*—Linda C. M. Dvorak
*Assistant Examiner*—Sonya C. Harris
*Attorney, Agent, or Firm*—Henry M. Feiereisen

[57] ABSTRACT

A micro surgical lighting instrument includes a hollow needle and a light guide received coaxially within the hollow needle and connected to a light source for transmitting light to a surgical site of a patient. The light guide has a distal end formed with an end face of circular segment shape and defined by a plane oriented orthogonal to the axis of the hollow needle, and a slanted surface adjacent the end face and extending rearwardly at an acute angle, with the slanted surface being lined by a coating for reflection of incident light rays.

14 Claims, 4 Drawing Sheets

LIGHTING INSTRUMENT, IN PARTICULAR FOR USE IN OPHTHALMOLOGIC MICROSURGERY

BACKGROUND OF THE INVENTION

The present invention generally relates to a lighting instrument for use in microsurgical procedures, in particular for use in ophthamologic microsurgery in the hyaloid or vitreous humor of the eye, and more particularly relates to a lighting instrument of a type including an optic light guide traversing a cannula or hollow needle and connected to a light source for insertion in a vessel or chamber of the vitreous humor of the eye.

In vitreous surgery, the use of ophthalmologic illuminating probes in form of optic light guides is proposed which are so designed at their tip as to enlarge the radiating light cone. Such light guides, or light guides that are further enhanced by being outfitted at their tip with a microscopic device or lens, provide oftentimes insufficient illumination of the chamber in the vitreous humor to allow a clear diagnosis or to perform a surgical procedure. Moreover, conventional light guides are incapable to provide sufficient illumination in the vitreous humor of the eye near the point of entry of the light probe into the eye. Conventional light probes provide also insufficient lighting of the retina especially in cases where the lighting has to be sufficiently extensive to provide lighting behind some bumps which can occur on the retina and which sometimes obstruct the light path. This situation occurs most frequently when the point of entry of the light guide is situated in the same quadrant of the vitreous humor as the region to be illuminated. Also, conventional light guides encounter the drawback that light rays are reflected in such a way that the surgeon or diagnostician is blinded by improperly reflected light rays, thus leading to imprecision and complications of the surgical procedures.

European Pat. No. EP-A 0 651 981 discloses a lighting probe for vitreous surgery, which is particularly adapted to enlarge the spatial angle of light radiating from the light guide, by constructing the tip of the light guide of frustoconical shape and with tapering exit area. Alternatively, the light guide is formed as a truncated cylinder which has one end face provided with a micro-optical element or lens.

Other conventional microsurgical instruments for illuminating a surgical site in a vessel or vitreous humor are disclosed e.g. in U.S. Pat. Nos. 4,733,937 and 4,551,129, which describe light guides that are formed at their ends where light exits with additional optical devices in the form of lenses or the like.

SUMMARY OF THE INVENTION

It is thus an object of the present invention to provide an improved lighting instrument with improved light guide, obviating the afore-stated drawbacks.

In particular, it is an object of the present invention to provide a light guide for a lighting instrument which is capable of focusing the radiating light bundle to a defined spatial angle to thereby eliminate unwanted and disturbing light reflections that affect surgical work.

These objects, and others which will become apparent hereinafter, are attained in accordance with the present invention by providing a hollow needle and a light guide received coaxially within the hollow needle and connected to a light source for transmitting light to a surgical site of a patient, with the light guide having a distal end formed with an end face of circular segment shape and defined by a plane oriented orthogonal to the axis of the hollow needle, and a slanted surface adjacent the end face and extending rearwardly at an acute angle, with the slanted surface being lined by a coating for reflection of incident light rays With a lighting instrument according to the present invention, a surgeon has now an implement in his or her hand that enables an illumination of the chamber of the vitreous humor in the direction of the optical axis of the light guide as well as in rearward and sideways directions so that the respectively selected quadrant of the vitreous chamber is illuminated in an optimum manner for surgical and diagnostic procedures. The straight as well as sideways light distribution is also advantageous because the available amount of light can be concentrated to substantially prevent glare that can bother the surgeon.

Suitably, the light guide may be surrounded by a cladding in direction of the axis, whereby the cladding is removed from the distal end of the light guide to expose it e.g. over an axial length of about 500 $\mu$m.

According to another feature of the present invention, the light guide has a core element defined by an outer diameter, with the circular segment shaped end face of the light guide having a vertical height which is smaller than half the diameter of the core element of the light guide.

Preferably, the slanted surface extends at an angle of 45° relative to an edge at a junction between the slanted surface and the end face and oriented transversely to the axis.

According to another feature of the present invention, the light rays exiting from the distal end of the light guide form a light cone defined by a flare angle as viewed in a plane of intersection, preferably a flare angle ranging from about 130° to 142°.

According to still another feature of the present invention, the hollow needle together with the light guide are rotatable within a cannula insertable in the pars plana of the eye about the axis and displaceable in direction of the axis relative to the pars plana of the eye for shifting the viewing range. The cannula is preferably provided in the form of a hollow-cylindrical tube for coaxially guiding the hollow needle, with the tube being formed with a flange for attachment to the sclera of the eye.

BRIEF DESCRIPTION OF THE DRAWING

The above and other objects, features and advantages of the present invention will now be described in more detail with reference to the accompanying drawing in which.

DETAILED DESCRIPTION OF PREFERRED EMBODIMENTS

Figure 1:
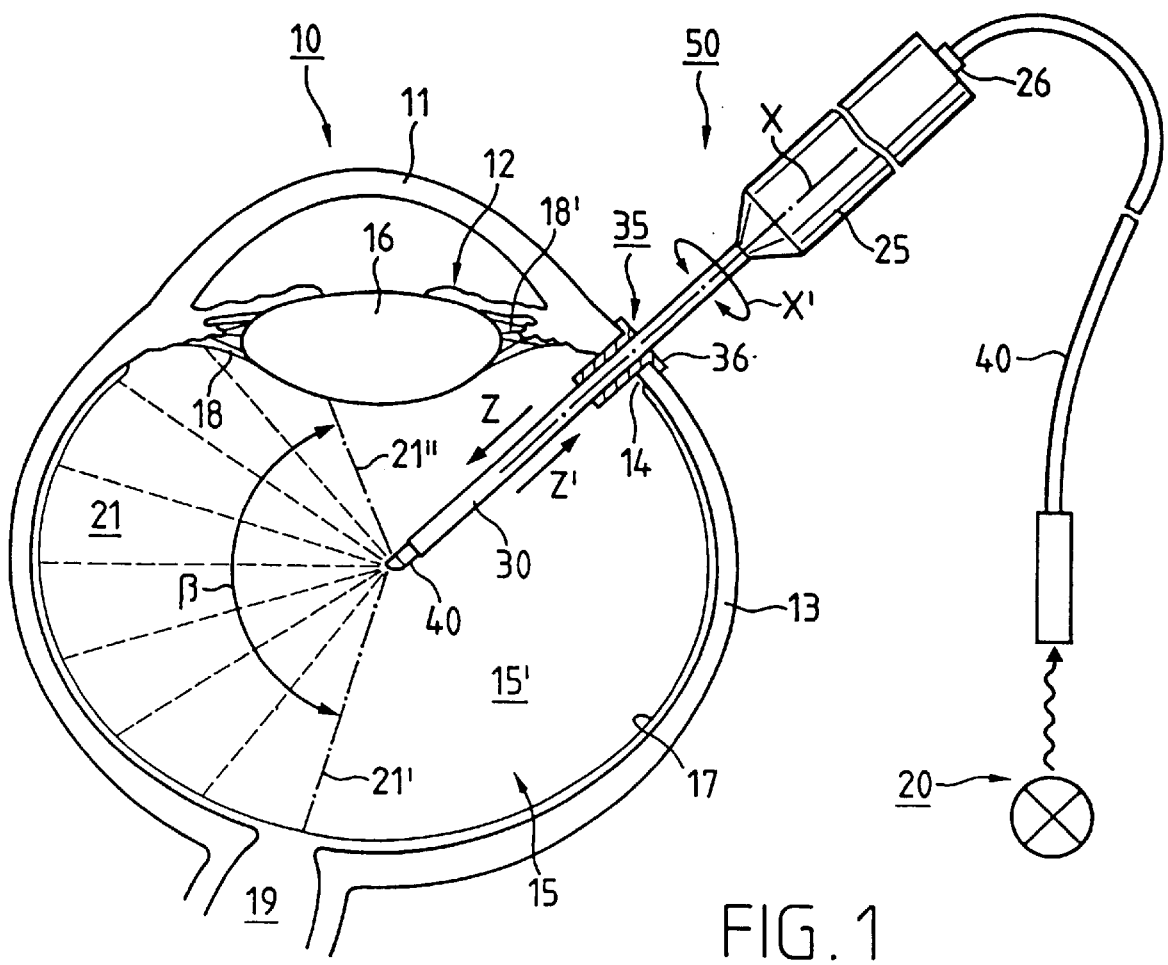
FIG. 1 is a horizontal section, on an enlarged scale, of a human eye during intraocular surgery with an optic light guide for a lighting instrument according to the invention inserted into the vitreous humor and depicted in a randomly selected first position.

Throughout all the Figures, the same or corresponding elements are generally indicated by the same reference numerals.

Turning now to the drawing, and in particular to FIG. 1, there is shown a horizontal section, on an enlarged scale, of a human eye, generally designated by reference numeral 10, and including the cornea 11, the iris generally designated by reference numeral 12, the sclera 13, the pars plana 14, the vitreous humor 15 with its vitreous chamber 15', the lens 16, the retina 17, the ciliary processes 18,18' (zonule fibers), and the optical nerve bundle 19.

Illumination of the chamber 15' of the vitreous humor 15 during surgery is effected by a lighting instrument, generally designated by reference numeral 50 for insertion in the area of the pars plana 14 into the eye 10. The lighting instrument 50 includes a hollow needle 30 and an optic light guide 40 which transmits light from a light source 20 to the surgical site and traverses the hollow needle 30 in direction of longitudinal axis X, with the longitudinal axis X of the lighting instrument 50 being essentially identical to the theoretic optical axis of the light guide 40. As shown in FIG. 1 by double arrow X', the lighting instrument 50 is rotatable about the longitudinal axis X and displaceable in axial direction as indicated by arrows Z, Z', without damaging the pars plana 14.

In the lighting instrument 50 of FIG. 1, the hollow needle 30 is received in a cannula 35 which is seated in an incision of the pars plana 14. The cannula 35 is formed on one end with a flange 36 for placement upon the sclera 13, thereby ensuring an exact and easier guidance of the light guide 40 being inserted together with the hollow needle 30 into the chamber 15' of the vitreous humor during rotation about axis X as well as movement in direction of arrows Z, Z'.

The hollow needle 30 can be positioned in any suitable location, with the light guide 40 emitting a light cone 21 which extends over a flare angle β of about 130° to 142° and is bounded by theoretic lines 21', 21". Thus, in the position of the lighting instrument 50 shown in FIG. 1, an entire quadrant of the chamber 15' of the vitreous humor 15 can be illuminated and covers an area reaching from the lens 16 or ciliary processes 18 to the optic nerve bundle 19 of the eye 10.

Figure 1A:
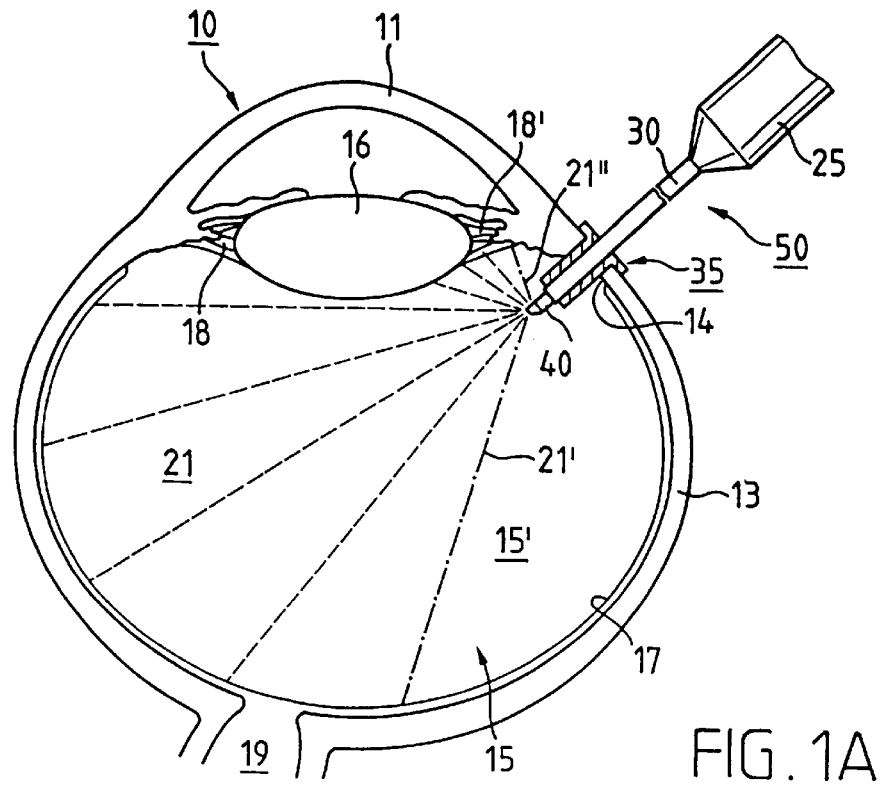
FIG. 1A is a horizontal section, on an enlarged scale, of the eye of FIG. 1, with the light guide being partially retracted from the vitreous humor into a second position.

FIG. 1A shows the lighting instrument 50 in a different selected position, with the hollow needle 30 and incorporated light guide 40 being retracted in axial direction Z' toward the point of entry near the pars plana 14. In this position, the light cone 21 radiating from the light instrument 50 illuminates a different second quadrant of the chamber 15', reaching from the ciliary processes 18' or pars plana 14 to the optic nerve bundle 19.

Figure 1B:
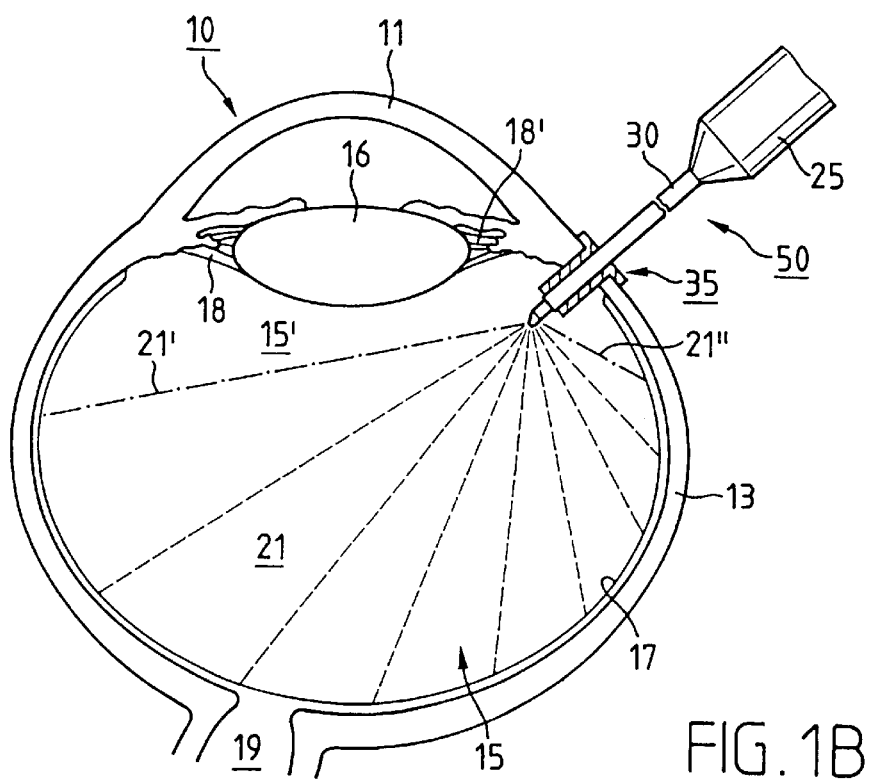
FIG. 1B is a horizontal section, on an enlarged scale, of the eye of FIG. 1, showing the light guide being partially retracted from the vitreous humor and rotated about its longitudinal axis.

FIG. 1B shows the light instrument 50 in the position of FIG. 1A, with the hollow needle 30 and the light guide 40 being rotated by e.g. 180° about the longitudinal axis X in direction of arrow X' (FIG. 1). In this position, the light cone 21 bounded by the theoretic lines 21, 21' illuminates a third quadrant of the chamber 15' of the vitreous humor 15, covering an area stretching from the equator (not shown here) of the eye 10 in direction of the optic nerve bundle 19.

It will be understood by persons skilled in the art that the positions of the lighting instrument 50 are shown in FIGS. 1, 1A and 1B by way of example only. Other positions of the lighting instrument 50 and the light guide 40 emitting the respective light cone 21 can be chosen as well, as a consequence of a positional adjustment in axial direction of arrows Z or Z' or rotation about axis X. Thus, it is possible to illuminate various quadrants and zones in the chamber 15' of the vitreous humor 15 and to completely illuminate in an optimum manner the retina 17, especially also regions within the vitreous humor 15 behind bumps or like elevations.

Figure 2:
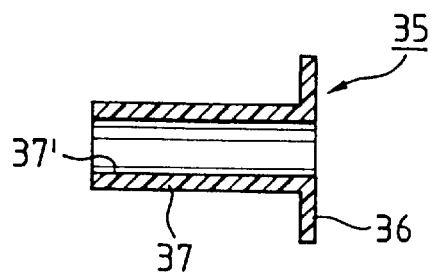
FIG. 2 is a sectional view, on an enlarged view, of a cannula for attachment to the light guide inserted in the area of the pars plana into the eye.

The cannula 35 for guiding the hollow needle 30 is shown on an enlarged scale in FIG. 2 and is formed from a tube 37 which has incorporated therein a bore 37' of a diameter complementing the outer diameter of the hollow needle 30. On one end thereof, the tube 37 is formed with the flange 36 for placement against the sclera 13.

Figure 3:
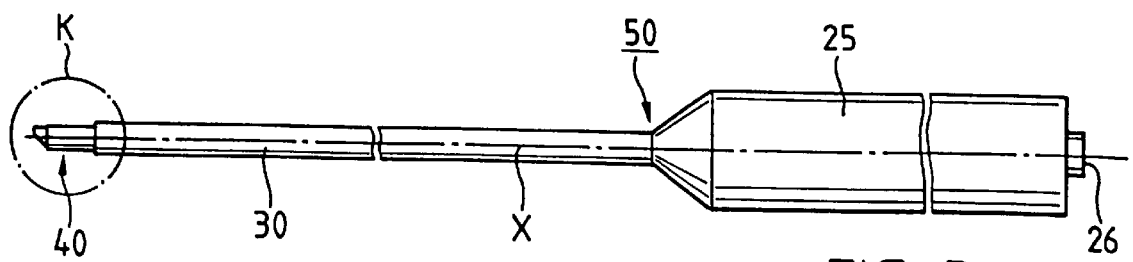
FIG. 3 is a side elevational view, on an enlarged scale, of a lighting instrument according to the present invention, including a light guide located within a hollow needle.

As best seen from FIG. 3, the lighting instrument 50 includes a housing 25 to form a grip. At one end thereof, the housing 25 is connected, preferably detachably, to the hollow needle 30. A fitting 26 is mounted to the other end of the housing 25 for attachment of the light guide 40 which transmits light from the light source 20 (FIG. 1). The hollow needle 30 is made from a tube of metal, e.g. stainless steel or any other inert material which is resistant to biological reactions.

Figure 4:
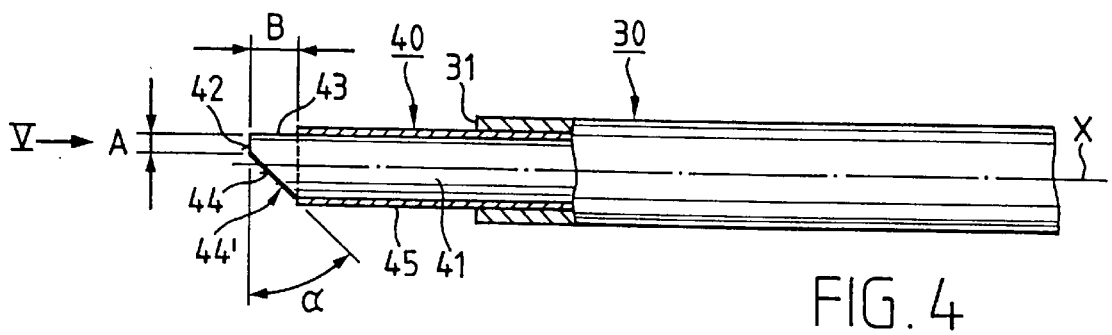
FIG. 4 is a cutaway side elevational view, on an enlarged scale, of a detail K, designated in FIG. 3, of the hollow needle accommodating a first embodiment of a light guide.

FIG. 4 is a cutaway side elevational view of a detail K of FIG. 3, showing in detail the front distal end (tip) of the hollow needle 30. The light guide 40 is made preferably from a monofilament having a light guide core 41 completely enveloped by a cladding or jacket 45. To achieve optimum light emission from the tip of the light guide 40, the cladding 45 is completely removed by any suitable tool from the front end of the light guide 40 over a length B of about 500 μm to expose the core 41 along section 43. This exposed section 43 of the core 41 terminates at the tip in an end face 42 which is of circular segment configuration and extends orthogonal to the theoretic optical axis X, as well as in a slanted surface 44 approximately in the form of a parabola which extends at an acute angle α, e.g. of 45°, with respect to the end face 42, with the slanted surface 44 extending rearwardly in direction of the proximal end face 31 of the hollow needle 30 and being lined by a coating 44'.

Figure 5:
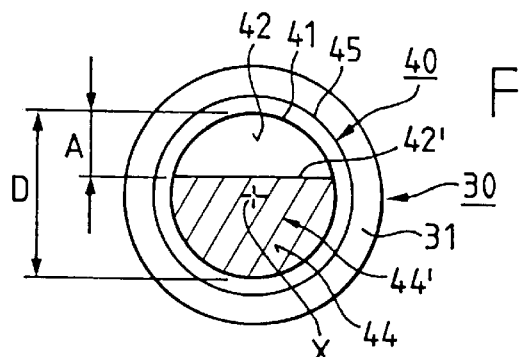
FIG. 5 is an enlarged front elevation view of the hollow needle, taken along arrow V in FIG. 4.

As illustrated in FIG. 5, the core 41 has an outer diameter D, with the circular segment shaped end face 42 exhibiting a vertical height A of about 250 μm. The vertical height A of the end face 42 is preferably smaller than half the diameter D of the core 41. The edge 42' which bounds the end face 42 oriented in a plane perpendicular to the longitudinal axis X, is situated, as seen in FIG. 5, at a vertical distance with respect to the optical longitudinal axis X.

Figure 6:
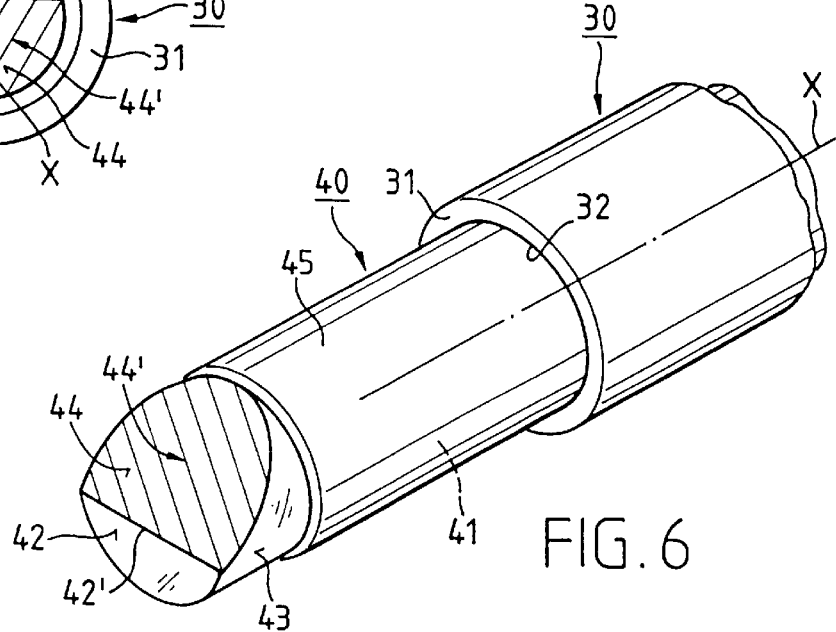
FIG. 6 is a front, top perspective view, on an enlarged scale, of the hollow needle of FIG. 4, with the light guide occupying a position rotated about its longitudinal axis.

FIG. 6 is a front, top perspective view, on an enlarged scale, of the hollow needle 30 of FIG. 4, with the light guide 40 occupying a position rotated about its longitudinal axis by 180°. The light guide 40 is received in a bore 32 of the hollow needle 30 and enveloped by the cladding or jacket 45. FIG. 6 shows also clearly the exposed section 43 of the core 41, with the end face 42 extending in a plane perpendicular to the longitudinal axis X as well as the slanted surface 44 extending rearwardly from the edge 42' which runs transversely to the longitudinal axis X.

Figure 7:
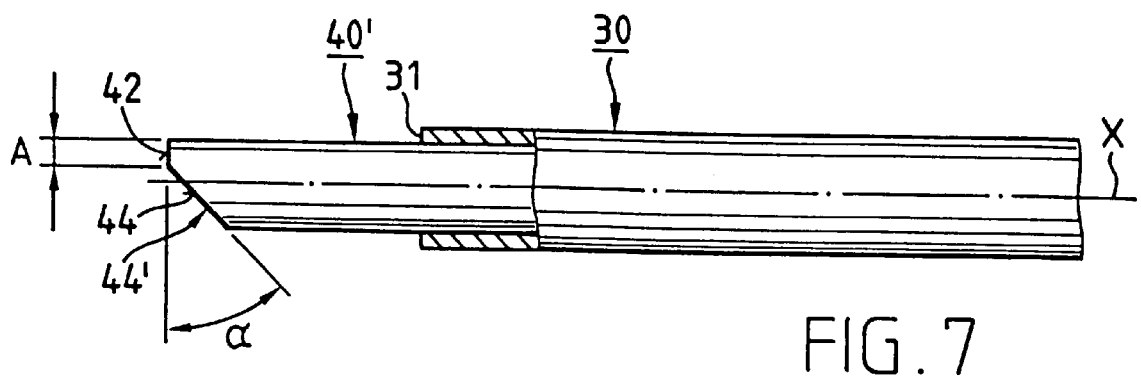
FIG. 7 is a fragmentary, partially sectional, side view, on an enlarged scale, of a hollow needle for use in a lighting instrument according to the present invention and accommodating a second embodiment of a light guide.
Figure 8:
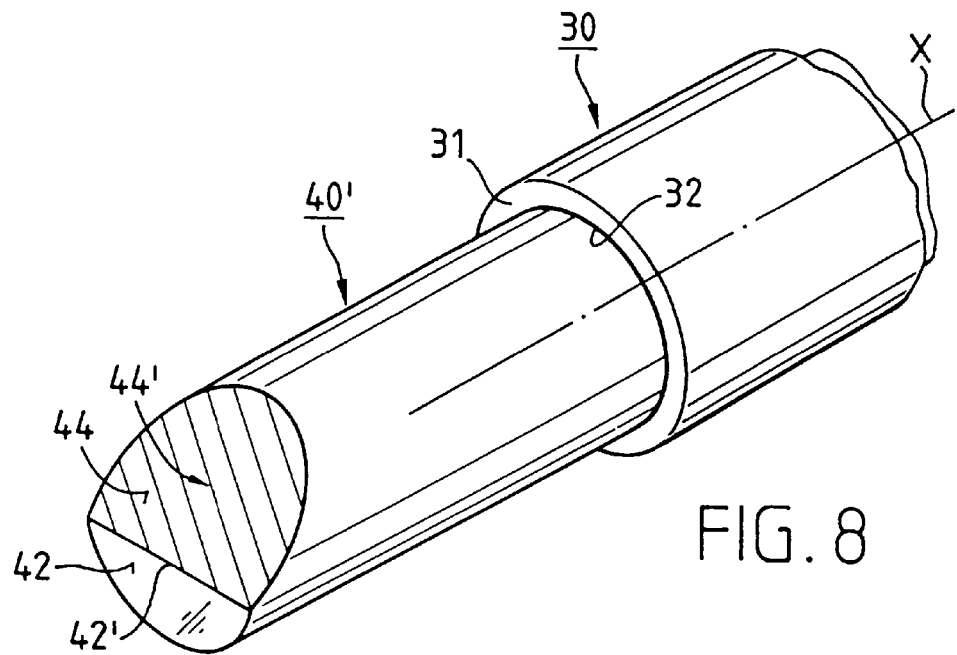
FIG. 8 is a front, top perspective view, on an enlarged scale, of the hollow needle of FIG. 7, with the light guide occupying a position rotated about its longitudinal axis.

Turning now to FIG. 7, there is shown a fragmentary, partially sectional, side view of the hollow needle accommodating coaxially therein a variation of a light guide, generally designated by reference numeral 40', with the difference between the light guide 40 of FIGS. 4 and 6 and the light guide 40' residing in the omission of a separate cladding or jacket for enveloping the core. Otherwise, the light guide 40' is identical to the light guide 40, with the front end of the light guide 40' having the circular segment shaped end face 42 and the slanted surface 44 extending rearwardly at an acute angle α from the end face 42 as well as the coating 44' applied on the surface 44. FIG. 8 is an enlarged perspective view of the lighting instrument 50 of FIG. 7, with the light guide 40' being rotated by e.g. 180° about the longitudinal axis X.

Persons skilled in the art will understand that light rays deflected by the end face 42 as well as by the rearwardly slanted surface 44 form together with the theoretic lines 21' and 21" the light cone 21. As schematically shown in FIGS. 1, 1A, 1B, the light cone 21 so emitted from the distal end of the light guide 40 or 40' describes a flare angle β, as viewed in the plane of section, of approximately 130° to 142°.

The light guide 40, 40' is made e.g. from conventional known plastic fiber material PMMA (polymethyl methacrylate). The circular segment shaped polished surface 44 adjacent the end face 42 and extending at an angle of preferably 45° is so constructed as to reflect incident light. Suitably, the reflecting property of the surface 44 can be accomplished by a coating 44', as indicated schematically in the drawing. The coating 44' is made from a material that is biologically inert and is preferably evaporated onto the slanted surface 44.

With the lighting instrument 50 according to the invention, the surgeon can modify the position of the radiating light cone 21, without additional means to thereby illuminate the desired viewing zone or quadrant of the chamber 15' of the vitreous humor 15 or body vessel.

While the invention has been illustrated and described as embodied in a lighting instrument, in particular for use in ophthalmologic microsurgery, it is not intended to be limited to the details shown since various modifications and structural changes may be made without departing in any way from the spirit of the present invention. What is claimed as new and desired to be protected by Letters Patent is set forth in the appended claims:

What is claimed is:

1. A microsurgical lighting instrument, in particular for vitreous surgery; comprising:

a hollow needle defining an axis;

a light guide received coaxially within the hollow needle and connected to a light source for transmitting light to a surgical site of a patient, said light guide having a distal end formed with an end face of circular segment configuration and defined by a plane oriented orthogonal to the axis of the hollow needle, and with a slanted surface adjacent the end face and extending rearwardly at an acute angle; and a coating applied on the slanted surface for reflection of incident light rays.

2. The lighting instrument of claim 1, and further comprising a cladding for surrounding the light guide in direction of the axis.

3. The lighting instrument of claim 1 wherein the light guide has a core element defined by an outer diameter, said circular segment shaped end face of the light guide having a vertical height which is smaller than half the diameter of the core element of said light guide.

4. The lighting instrument of claim 3 wherein the vertical height is approximately 250 μm, said slanted surface having a shape in the form of a parabola.

5. The lighting instrument of claim 2 wherein the cladding is removed from the distal end of the light guide over an axial length of about 500 μm.

6. The lighting instrument of claim 1 wherein an edge is formed at an interface between the slanted surface and the circular segment shaped end face and extending transversely to the axis, said slanted surface extending at an angle of 45° relative to the edge.

7. The lighting instrument of claim 1 wherein the coating deposited on the slanted surface is made of biologically inert material.

8. The lighting instrument of claim 7 wherein the coating is evaporated onto the slanted surface.

9. The lighting instrument of claim 1 wherein the light rays emitted from the distal end of the light guide form a light cone defined by a flare angle as viewed in a plane of intersection.

10. The lighting instrument of claim 9 wherein the flare angle ranges from about 130° to 142°.

11. The lighting instrument of claim 1, and further comprising a cannula insertable in the pars plana of the eye for receiving and guiding the hollow needle.

12. The lighting instrument of claim 1 wherein the hollow needle together with the light guide are rotatable about the axis and displaceable in direction of the axis relative to the pars plana of the eye for shifting a viewing range.

13. The lighting instrument of claim 1, and further comprising a cannula insertable in the pars plana of the eye for receiving and guiding the hollow needle, said hollow needle being rotatable within the cannula.

14. The lighting instrument of claim 11 wherein the cannula is provided in the form of a hollow-cylindrical tube for coaxially guiding the hollow needle, said tube being formed with a flange for attachment to the sclera of the eye.

* * * * *